Figure 1:
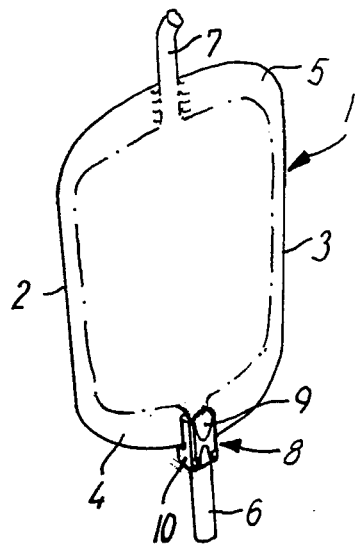

United States Patent [19]

Kamstrup-Larsen et al.

[11] Patent Number: 4,736,925
[45] Date of Patent: Apr. 12, 1988

[54] HOSE CLAMP FOR AN OUTLET HOSE MEMBER FROM A LIQUID COLLECTION BAG

[75] Inventors: Jørgen Kamstrup-Larsen, Allerød; Michael Morris, Copenhagen, both of Denmark

[73] Assignee: Coloplast A/S, Denmark

[21] Appl. No.: 75,058

[22] PCT Filed: Sep. 30, 1986

[86] PCT No.: PCT/DK86/00110
§ 371 Date: Jun. 29, 1987
§ 102(e) Date: Jun. 29, 1987

[87] PCT Pub. No.: WO87/02575
PCT Pub. Date: May 7, 1987

[30] Foreign Application Priority Data

Oct. 30, 1985 [DK] Denmark .............................. 4986/85

[51] Int. Cl.⁴ .................... A61F 5/44; F16L 55/19; F16K 7/06
[52] U.S. Cl. ......................................... 251/10; 251/4; 604/34
[58] Field of Search .................. 251/4, 9, 10; 604/34, 604/250

[56] References Cited

U.S. PATENT DOCUMENTS 3,942,228 3/1976 Buchman et al. ............... 251/10 X
4,051,578 10/1977 Manschot et al. ............... 251/4
4,643,389 2/1987 Elson et al. ...................... 251/10

Primary Examiner—A. Michael Chambers
Assistant Examiner—John C. Fox
Attorney, Agent, or Firm—Ostrolenk, Faber, Gerb & Soffen

[57] ABSTRACT

A hose clamp (8) to be positioned on an outlet hose member (7) from a liquid collection bag (1), e.g. a urine collection bag, is provided with two hingedly connected clamp parts (9, 10), one of which (10) has a U-shaped cross-section and lateral portions (13, 14), including longitudinal slots (15) to receive the bottom portion (4) of the bag (1). When mounted, the clamp (8) is pushed onto the bottom portion (4) of the bag (1) so that only a small part of the clamp (8) extends outside the bag. Thereby, the inconveniences to the user are diminished to the largest extent and an improved security against unintentional opening is obtained.

5 Claims, 1 Drawing Sheet

HOSE CLAMP FOR AN OUTLET HOSE MEMBER FROM A LIQUID COLLECTION BAG

The invention relates to a hose clamp to be positioned on an outlet hose member inserted at the bottom of a liquid collection bag between welded wall portions of the bag, comprising two clamp parts that are hingedly connected at one end and one of which is provided with a jaw part that is eccentric about the hinge axis and, in the closing position of the clamp, squeezes the hose member against a stationary jaw part on the second clamp portion, the clamp parts having releasable locking means active in the closing position.

Such hose clamps are mainly used in liquid collection bags for medical or hygienic purposes, e.g. urine collection bags for incontinence equipments.

For emptying such bags it is known to make use of a rigid socket accommodating a valve as well as a resilient hose member, the latter being considerably more suitable with regard to the comfort of the user.

With respect to the closing member of such an outlet hose member it is a primary demand that it ensures in its closing position a completely leakage-free squeezing of the hose member. Moreover, the closing member should as far as possible be secured against unintentional opening and simultaneously it must not be too difficult to open when emptying is to take place.

In known urine collection bags hose clamps of a conventional design mounted on the part of the outlet hose member extending outside the bag are used. As the hose clamp is made from a rigid material it is frequently irritating to the user and thus does not fulfil the wish to better comfort which is the mere reason for applying a flexible hose member. Such inconveniences apply in particular, if the clamp extends transversely of the longitudinal direction of the hose member in order to keep the hose member proper as short as possible.

The fact that the clamp parts are located freely outside the bag proper makes it further difficult to combine the actually contradictory demands on a reliable locking in the closing position and on a handy opening ability.

It is the object of the invention to provide a hose clamp that does not suffer from these functional drawbacks of known closing means.

To accomplish this, the hose clamp according to the invention is characterized in that said second part has a substantially U-shaped cross-section corresponding to the outer diameter of the hose member and having lateral portions in which opposite longitudinal slots for receiving said welded wall portions of the bag are provided, said slots extending from the end opposite the hinge connection through such a length of the clamp that only a slight portion thereof around the jaw parts projects outside the edge of said wall portions.

The design of one of the clamp portions as a U-shaped member which on the major part of its length by means of said slots is pushed onto the welded bottom walls of the bag so that only a very small portion of the clamp projects outside the bag, entails a considerably improved comfort to the user.

Moreover, since in the closing position also said one clamp part superposes the bag in engagement with the U-shaped part, the clamp is considerably better protected against, i.e. less accessible to unintentional opening.

Figure 2:
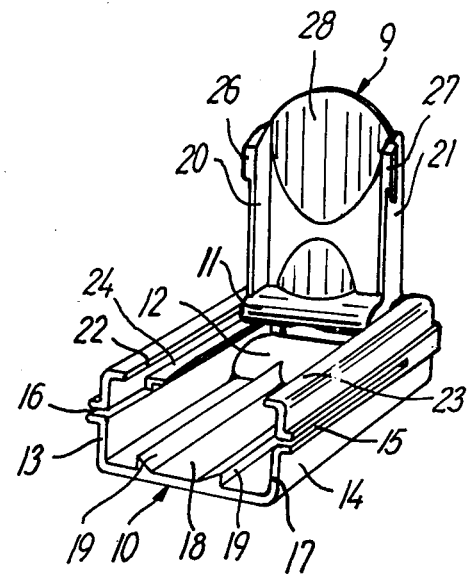
Figure 4:
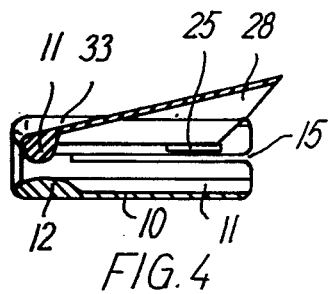
Figure 5:
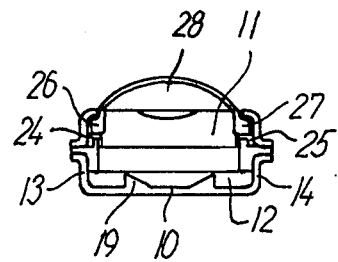
Figure 3:
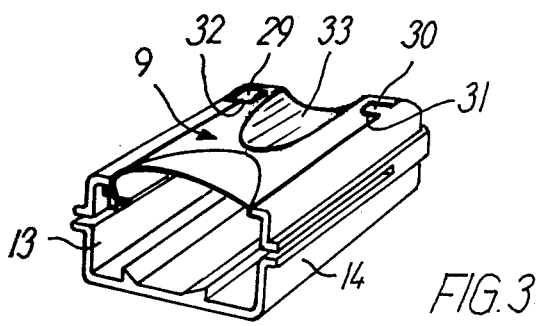

The invention will now be explained in detail by means of an embodiment illustrated in the drawings, in which FIG. 1 shows a hose clamp according to the invention mounted on a urine collection bag, FIGS. 2 and 3 are perspective views of the hose clamp in open and closed positions, respectively, FIG. 4 is a longitudinal view, and FIG. 5 illustrates the hose clamp from one end.

The urine collection bag shown in FIG. 1 is of a conventional design with resilient walls made from plastic material, said walls being welded together in a liquidtight manner at lateral portions 2 and 3, a bottom portion 4 and a top portion 5, an outlet hose member 6 and an inlet hose member 7, respectively, being inserted, however, between the welded bag walls at the bottom portion 4 and the top portion 5, of which the inlet hose member may for instance be connected with an external catheter of the kind disclosed in published international patent application No. WO 86/00816.

A hose clamp 8 to be further described in the following is mounted around the outlet hose member 6. In the illustrated mounted position the clamp 8 is pushed onto the bottom portion 4 of the bag 1 surrounding the portion of the outlet hose member 6 located between the bag walls so that only a very little portion of the clamp 8 extends outside the bag 1.

As illustrated in FIGS. 2 to 5 the clamp 8 comprises two clamp parts 9 and 10 that are hingedly connected at the one end which in the mounted position of the clamp projects outside the bag. In a manner known per se the first hinge part 9 is provided with a jaw part 11 which is eccentric with respect to the hinge axis and, in the closing position, squeezes the hose member 6 against a stationary jaw part 12 on the second clamp part 10.

As it appears most clearly from FIG. 4, the clamp part 10 has a substantially U-shaped cross-section corresponding to the outer diameter of the hose member 6 and includes lateral portions 13 and 14 in which longitudinal slots 15 and 16 are provided to receive the bottom portion 4 of the bag 1, said slots extending from the end edge 17 opposite the hinged connection through such a length of the clamp 8 that only a slight portion thereof around the hinge connection projects outside the bag 1 as illustrated in FIG. 1.

The bottom 18 of the U-shaped clamp part 10 may be provided with upwardly projecting, longitudinal ribs 19 serving as guide members for the hose member 6.

For locking the clamp 8 in the closing position illustrated in FIGS. 1, 3 and 4 the lateral portions 13 and 14 of the U-shaped clamp part 10 and inwardly projecting edge portions 20 and 21 of the clamp part 9 are provided with engaging parts which in the illustrated example are constituted by inwardly projecting edge portions 22 and 23 and underlying, longitudinal rib projections 24 and 25 on the lateral portions 13 and 14 and parallel to said edge portions, and by outwardly projecting protuberances 26 and 27 at the free end of each of the edge portions 20 and 21 of the clamp part 9. Said engaging parts provides for obtaining in the closing position a reliable snap locking engagement between the clamp parts 9 and 10, the external surface of the clamp part 9 flushing substantially with the top edges of the lateral portions 13 and 14 of the clamp part 10.

In order to facilitate the opening the clamp part 9 may at its end opposite the hinge connection be formed with an outwards directed bulge 28 constituting a handy finger grip.

In the illustrated example, as it appears from FIG. 5, the hinge connection between the clamp parts 9 and 10 is provided by engagement between inwardly projecting hinge pins 29 and 30 on the lateral portions 13 and 14 of the clamp part 10 and matching recesses 31 in the external surface of the clamp part 9 at the jaw part 11.

Between the recesses 31 and 32 the clamp part 9 comprises a conical depression 33 which in the open position of the hose clamp with the clamp part 9 turned substantially 180° in relation to the closing position, causes that the squeezing effect on the hose member becomes minimum, thereby ensuring a maximum free liquid flow through the hose member when emtying the bag 1 through the hose member.

Each of the clamp parts 9 and 10 may be formed in one piece, for instance from an injection moulded plastic material.

We claim:

1. A hose clamp to be positioned on an outlet hose member inserted at the bottom of a liquid collection bag between welded wall portions of the bag, comprising two clamp parts that are hingedly connected at one end and one of which is provided with a jaw part that is eccentric with respect to the hinge axis and, in the closing position of the clamp, squeezes the hose member against a stationary jaw part on the second clamp part, the clamp parts having releasable locking means active in the closing position, said second clamp part has a substantially U-shaped cross-section corresponding to the outer diameter of the hose member and has lateral portions in which opposite longitudinal slots for receiving said welded wall portions of the bag are provided, said slots extending from the end opposite the hinge connection through such a length of the clamp that only a slight portion thereof around the jaw parts projects outside the edge of said wall portions.

2. A hose clamp as claimed in claim 1, wherein that said lateral portions of the second clamp part are provided with said locking means for mutual snap locking of said two parts in the closing position, the external surface of said one part lying substantially flush with the top edges of said lateral portions.

3. A hose clamp as claimed in claim 2, wherein in that said one part at its end opposite the hinge connection is formed as a finger grip.

4. A hose clamp as claimed in claim 2, wherein that said one part in the area of the hinge connection has a conical depression in its external surface to ensure a maximum free liquid flow through the hose member in the fully open position of the clamp.

5. A hose clamp as claimed in claim 3, wherein said one part in the area of the hinge connection has a conical depression in its external surface to ensure a maximum free liquid flow through the hose member in the fully open position of the clamp.

* * * * *